US006475748B1

(12) United States Patent
Majima et al.

(10) Patent No.: US 6,475,748 B1
(45) Date of Patent: Nov. 5, 2002

(54) METHOD FOR DIFFERENTIATING HUMAN PERIPHERAL BLOOD GRANULOCYTES

(75) Inventors: Toshiro Majima, Yokohama (JP); Ryoichi Nagatomi, Sendai (JP); Tasuke Konno, Sendai (JP); Toshikazu Awataguchi, Sendai (JP); Yoshimi Yano, Sendai (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 08/243,080

(22) Filed: May 16, 1994

Related U.S. Application Data

(63) Continuation of application No. 07/969,337, filed on Oct. 30, 1992, now abandoned.

(30) Foreign Application Priority Data

Apr. 30, 1992 (JP) ............................................. 4-111555

(51) Int. Cl.[7] .............................................. G01N 33/53
(52) U.S. Cl. .................. 435/7.24; 435/7.21; 435/240.2; 435/811; 435/968; 436/63; 436/520; 436/536; 436/547; 436/811
(58) Field of Search .............................. 435/7.21, 7.24, 435/240.2, 811, 968; 436/63, 520, 536, 547, 811

(56) References Cited

U.S. PATENT DOCUMENTS 5,108,899 A    4/1992   Allen .......................... 435/7.21

OTHER PUBLICATIONS

Majima et al, 1990. Unusual Expression of IgG Fc Receptors on Peripheral Granulocytes from Patients with Leukocyte Adhesion Deficiency (CD11/CD18 Deficiency). J Immunol 145: 1694–9.*

Guyre et al, 1990. Monocytes and Polymorphonuclear Neutrophils of Patients with Streptococcal Pharyngitis Express Increased Numbers of Type I IgG Fc Receptors. J Clin Invest. 86:1892–6.*

Yancey et al, 1985. Human C5a Modulates Monocyte Fc and C3 Receptor Expression. J Immunol 135: 465–470.*

Werfel et al, 1989. Fc and Complement Receptors are Increased on Human Peripheral Granulocytes and Monocytes but not on Lymphocytes in Response to C5a. FASEB J 3(4): A1087, Abstract #4999.*

Matsumoto et al, 1987. Augmentation of Antibody–Dependent Cellular Cytotoxicity of Polymorphonuclear Leucocytes by Interferon–Gamma: Mechanism Dependent on Enhancement of Fc Receptor Expression and Increased Release of Activated Oxygens. Chem. Pharm. Bull. (Tokyo) 35(4): 1571–78.*

Van de Winkel et al, 1988. Selective Modulation of Two Human Monocyte Fc Receptors for IgG by Immobilized Immune Complexes. J Immunol. 140: 3515–21.*

Majima et al., *Proc. Jpn. Soc. Immunol.*, vol. 21, 1991.

* cited by examiner

*Primary Examiner*—Christopher L. Chin
(74) *Attorney, Agent, or Firm*—Bacon & Thomas

(57) ABSTRACT

Disclosed is a method for differentiating human peripheral blood granulocytes which comprises cultivating the granulocytes in the presence of an interferon and acting an immune complex on said granulocytes in the presence of a chemiluminescent substance, and measuring the chemiluminescent amounts induced. It contributes to the screening of patients suffering from serious infectious diseases or a range of inflammations, and is advantageous for monitoring the curative effects for those patients.

2 Claims, No Drawings

METHOD FOR DIFFERENTIATING HUMAN PERIPHERAL BLOOD GRANULOCYTES

This application is a Continuation of application Ser. No. 07/969,337, filed Oct. 30, 1992, now abandoned.

BACKGROUND OF THE INVENTION

1. Field of the Invention

The present invention relates to a method for differentiating human peripheral blood granulocytes, and, more particularly, to a method for determining human peripheral blood granulocytes whether in a healthy person, or in those suffering from serious infectious diseases or inflammatory diseases, and the like.

2. Description of the Background Art

There have been practically no accurate methods for diagnosing or reliable methods for monitoring the patients who are suffering from an acute, subacute, or chronic inflammatory disease or a serious infectious disease, such as chronic tonsillitis, Crohn's disease, agammaglobulinemia, ulcerative colitis, septicemia, leukemia, leukocyte adherence deficiency; or those who had undergone a kidney transplant. Development of an accurate diagnostic method and a monitoring method which can easily be applied for the evaluation of the curative effects for those patients have therefore been in demand.

In view of this situation, the present inventors have undertaken extensive studies on the relationship between the features of human peripheral blood granulocytes and various inflammatory diseases, and have found that an IgG.Fc receptor I (hereinafter referred to as "IgG.FcRI") is scarcely present on the surface of human peripheral blood granulocytes of healthy persons, whereas it is evidently recognized on those of patients suffering from inflammatory diseases or the like. Further investigations have revealed that the IgG.FcRI can be recognized in vitro by acting an interferon on peripheral blood granulocytes. Based on this fact, it has been elucidated that IgG.FcRI on human peripheral blood granulocytes can be quantified by a method which comprises i) cultivating the granulocytes in the presence of an interferon, ii) acting an immune complex on the granulocytes in the presence of a chemiluminescent substance, and to induce IgG.FcRI presence on the granulocytes, and iii) measuring the intensified photon quantity generated by the stimulation of IgG.FcRI appearing on the granulocytes using a chemiluminescence method (hereinafter referred to as "CL"). This differentiation method is believed to contribute to the diagnoses of patients suffering from either an serious infectious disease or any one of the inflammatory diseases, and is advantageous for monitoring the curative effects of those patients. These findings have led to the completion of the present invention.

SUMMARY OF THE INVENTION

Accordingly, an object of the present invention is to provide a method for differentiating human peripheral blood granulocytes which comprises: cultivating the granulocytes in the presence of an interferon, acting an immune complex on the granulocytes in the presence of a chemiluminescent substance, and measuring the chemiluminescent quantities induced.

In a preferred embodiment, a human interferon-gamma is used as said interferon, and a complex containing mouse IgG is used as said immune complex.

Other objects, features and advantages of the invention will hereinafter become more readily apparent from the following description.

DETAILED DESCRIPTION OF THE INVENTION AND PREFERRED EMBODIMENTS

The human peripheral blood granulocytes to be used in the present invention can be human peripheral blood as is, or granulocytes separated from peripheral blood. Separation of human peripheral blood granulocytes from human peripheral blood can be carried out according to a known method, for example, stratifying heparin blood or EDTA blood in a "Mono-poly resolving medium" and subjecting it to centrifugation.

"Mono-poly resolving medium" is a trademark of Flow Lab. Co., and it names a medium which can resolve the mono- form from the poly- form.

As an interferon (hereinafter referred to as "IFN") used in the present invention, a human IFN-gamma is preferable, which includes those prepared from human lymphocytes, as well as recombinant IFN obtained by gene recombination techniques.

Luminol, lucigenin, luciferin, or the like, and their derivatives can be given as examples, but not limiting thereof, of the chemiluminescent substances to be used in the present invention.

The immune complexes used in this invention include a complex containing mouse IgG, for example, a complex in which mouse IgG and sheep red blood cells (hereinafter referred to as "SRBC") are bonded chemically, a mixture of anti-SRBC-mouse IgG and SRBC, a complex of mouse IgG and latex, a complex of mouse IgG and various proteins, a complex of mouse IgG and various saccharides or polysaccharides, and the like. Specifically, a monoclonal or polyclonal mouse $IgG_{2a}$ is particularly preferable as the mouse IgG to be used.

In the practice of this invention, the human peripheral blood or the granulocytes thereof is first dispersed in an RPMI medium which contains 15% FCS, and then 10–1000 U/ml, preferably 100 U/ml, of IFN is added to the dispersion, followed by cultivation for 10–20 hours. To this culture, an appropriate amount of a chemiluminescent substance, which is dissolved in dimethylsulfoxide or the like and being diluted with a phosphate saline buffer (hereinafter referred to as "PBS"), and an immune complex are added in order to measure the quantity of chemiluminescence induced. In this instance, luminol is added as a preferable chemiluminescent substance at a concentration between $1\times10^{-3}$–$1\times10^{-6}$M and an IgG-SRBC complex as a preferable immune complex in an amount equivalent to 30 times to the number of granulocytes.

Differentiation of the subject granulocytes can be achieved by comparing the chemiluminescent values of those IFN-added and IFN-not added. For instance, the ratio of chemiluminescence amounts (hereinafter referred to as "CL ratio") can be calculated according to the following equation:

$$CL\ ratio = \frac{\text{Peak luminescence counts of the culture in which } IFN \text{ was not added}}{\text{Peak luminescence counts of the culture in which } IFN \text{ was added}}$$

In this equation, a large CL ratio indicates that the granulocytes inspected are those of patients suffering from inflammation or the like, whereas a small CL ratio denotes that the granulocytes inspected are those of healthy person.

Other features of the invention will become apparent in the course of the following description of the exemplary embodiments which are given for illustration of the invention and are not intended to be limiting thereof.

EXAMPLES

Example 1

(1) Preparation of Human Peripheral Blood

The peripheral blood of a healthy person or a patient was collected by using heparin or EDTA, followed by dilution with an RPMI medium containing 15% FCS to 100-fold in volume. The diluted blood was distributed into a 96-well microplate in an amount of 100 μl/well.

(2) Separation and Preparation of Human Peripheral Blood Granulocytes 5 ml of heparin blood or EDTA blood was stratified in a "Mono-poly resolving medium" and centrifuged at room temperature for 30 minutes at 400 g. The granulocytes thus obtained were washed three times with a cold RPMI-1640 medium, followed by dilution with an RPMI medium containing 15% FCS to a concentration of $1\times10^6$ cells/ml, and 100 μl of which was served for the succeeding test.

(3) Preparation of Interferon

A recombinant IFN-gamma (manufactured by Shionogi Pharmaceutical Co., $1\times10^7$ U/mg protein) was dissolved in PBS and stored at $-80°$ C. at a concentration of $1\times10^5$ U/ml. This IFN-gamma is dissolved prior to use and diluted with PBS at a concentration of $1\times10^3$ U/ml.

(4) Preparation of Immune Complex 0.5 ml of fresh SRBC (purchased from Denka Seiken) was subjected to centrifugal washing at 2,500 rpm for 5 minutes, followed by dispersion in 1 ml of PBS. 1 ml of trinitro-benzene sulfonic acid (hereinafter referred to as "TNP") solution dissolved in PBS (concentration: 3 mg/ml) was added to 1 ml of SRBC, and the mixture was reacted at 37° C. for 15 minutes with shaking. The reactant mixture was washed once with PBS, and washed twice by centrifugation with gelatin-veronal buffer (containing $Ca^{++}$, $Mg^{++}$; hereinafter referred to as "$GVB^{++}$"), and dispersed in $GVB^{++}$ at a concentration of $2\times10^9$ cells/ml. This dispersion is hereinafter referred to as "TNP-SRBC."

After an addition of 0.2 ml of the TNP-SRBC dispersion to 4 ml of $GVB^{++}$, the mixture was sensitized with an antibody, anti-TNP.mouse $IgG_{2a}$ or anti-TNP.mouse $IgG_{2b}$, at a sub-agglutinative concentration (at 37° C. for 30 minutes). This TNP-SRBC sensitized by mouse IgG is hereinafter referred to as "mouse IgG-TNP-SRBC." The mouse IgG-TNP-SRBC was then washed three times with $GVB^{++}$, followed by dispersion in 2 ml of $GVB^{++}$ ($2\times10^8$ cells/ml).

(5) Preparation of Chemiluminescent Substance

Luminol was dissolved in dimethylsulfoxide (hereinafter referred to as "DMSO") to make a solution having a concentration of 1.8 mg/100 μl, followed by dilution with PBS to adjust the concentration to $1\times10^{-3}$ M, and stored at $-20°$ C. Lucigenin was dissolved in distilled water and diluted with PBS to adjust its concentration to $1\times10^{-2}$ M, and stored at $-20°$ C. Similarly, luciferin was dissolved in distilled water and diluted with PBS to adjust its concentration to 100 μg/ml, and stored at $-20°$ C. These substances were dissolved prior to use, and their final concentrations were adjusted to $1\times10^{-4}$–$10^{-5}$ M for luminol and lucigenin respectively, and 0.1–10 μg/ml for luciferin.

(6) Measurement of Chemiluminescent Amount

The peripheral blood granulocytes of 21 healthy persons, six patients suffering from chronic tonsillitis, and four patients who once suffered from chronic tonsillitis and underwent tonsillectomy were collected separately by the method described in 2) above. Each of these granulocytes prepared was distributed into a 96-well microplate and 10 μl of the interferon prepared in 3) above was added, followed by cultivation in a $CO_2$ incubator for 18 hours at 37° C. To the culture was added 10 μl of luminol prepared in 5) above and the amount of chemiluminescence of each subject was measured using ML-1000 equipment manufactured by Dynatech. Further, after the addition of 10 μl of the immune complexes or TNP-SRBC to each sample, the chemiluminescent amounts of these samples were measured. The results are presented in Table 1.

TABLE 1

| Subjects | CL ratio |
| --- | --- |
| Healthy person (n = 21) | 0.11 ± 0.10 |
| Patients of chronic tonsillitis: | |
| 1) before tonsillectomy (n = 6) | 0.77 ± 0.30 |
| 2) 1 week after tonsillectomy (n = 4) | 0.43 ± 0.36 |

Example 2

The chemiluminescent amount of the peripheral blood of a patient suffering from leukocyte adherence deficiency was measured and compared according to the method described in Example 1, by preparing two test samples: 1) 100 μl of 100-fold dilution of the whole peripheral blood, and 2) the granulocytes prepared from said peripheral blood. The test results are given in Table 2.

TABLE 2

| Subjects | CL ratio |
| --- | --- |
| Patient with leukocyte adherence deficiency: | |
| 1) whole peripheral blood | 0.56 |
| 2) granulocytes | 0.64 |

Example 3

The peripheral bloods of eight patients suffering from agammaglobulinemia and two patients suffering from leukemia were subjected to the test. The chemiluminescent amounts of their granulocytes were measured and compared according to the method described in Example 1. The test results are presented in Table 3.

TABLE 3

| Subjects | CL ratio |
| --- | --- |
| Patients with agammaglobulinemia (n = 8) | 0.1–1.0 |
| Patients with leukemia (n = 2) | 0.6–0.7 |

Reference Example 1

Examination of the Amount of the Interferon to be Added

The granulocytes separated from a healthy person by the method described in Example 1-(2) were cultivated in the presence of 0.1, 1, 10, 100, 1000 U/ml of IFN prepared in Example 1-(3). The CL ratios of luminol measured by the method described in Example 1-(6) exhibited a dependency on the concentrations of IFN, with the minimum CL ratio being 0.8.

The test results on a different healthy person also showed a similar dependency, and eventually the optimum concentration of IFN to be added was found to be 100 U/ml. Further, the tests using lucigenin gave similar results.

Reference Example 2
Examination of the Cultivation Period of the Interferon To the granulocytes separated from a healthy person by the method described in Example 1-(2) was added 100 U/ml of IFN prepared in Example 1-(3), and its chemiluminescent amount was measured by the method described in Example 1-(6). The CL ratio of luminol was 0.5 after 6-hours cultivation, 0.2 after 12-hours cultivation, and exhibited a minimum value of 0.1 after 15 to 18-hours cultivation.

Reference Example 3
Examination of the Necessity for Interferon Addition To the granulocytes separated from a healthy person by the method described in Example 1-(2) was added a mixture of recombinant-human IL1, IL2, IL3, IL6, GCSF, TNF, IFN-alpha, IFN-gamma and various cytokines with different concentrations, followed by cultivation for 18 hours. The chemiluminescent amount of each sample was measured by the method described in Example 1-(6) to determine the occurrence of IgG.FcRI, in which only IFN-gamma among all of the cytokines used showed an increase in IgG.FcRI response.

As can be seen, the method of this invention greatly contributes to the screening of patients suffering from serious infectious diseases or a range of inflammations, and is advantageous for monitoring the curative effects for those patients.

Obviously, numerous modifications and variations of the present invention are possible in light of the above teachings. It is therefore to be understood that within the scope of the appended claims, the invention may be practiced other than as specifically described herein.

What is claimed is:

1. A method for detecting infectious or inflammatory disease in a human patient who is suspected of having inflammation or infection resulting from kidney transplant which method comprises:
    (a) quantifying IgG-FcRI receptors on human peripheral blood granulocytes derived from the patient by:
        (1) cultivating the granulocytes in the presence of human interferon-y;
        (2) reacting the cultivated granulocytes from step (a)(1) with an immune complex comprising mouse IgG and a chemiluminescent substance to generate chemiluminescence; and
        (3) measuring intensity of the chemiluminescence generated;
    (b) quantifying IgG-FcRI receptors on human peripheral blood granulocytes derived from the patient by:
        (1) cultivating the granulocytes in the absence of human interferon-y;
        (2) reacting the cultivated granulocytes from step (b)(1) with an immune complex comprising mouse IgG and a chemiluminescent substance to generate chemiluminescence; and
        (3) measuring intensity of the chemiluminescence generated;
    (c) calculating a CL ratio, which is the ratio of the intensity of the chemiluminescence generated in step (b) to the intensity of the chemiluminescence generated in step (a); and
    (d) comparing the CL ratio obtained in step (c) to a CL ratio of a healthy human subject, so as to detect the presence of infectious or inflammatory disease in the patient.

2. A method of monitoring the curative effects on infectious or inflammatory disease in a human patient, which method comprises obtaining from the patient at least two samples of human peripheral blood granulocytes at intervals of time, subjecting the samples to a method for detecting infectious or inflammatory disease in a human patient, which method comprises:
    (a) quantifying IgG-FcRI receptors on human peripheral blood granulocytes derived from the patient by:
        (1) cultivating the granulocytes in the presence of human interferon-y;
        (2) reacting the cultivated granulocytes from step (a)(1) with an immune complex comprising mouse IgG and a chemiluminescent substance to generate chemiluminescence; and
        (3) measuring intensity of the chemiluminescence generated;
    (b) quantifying IgG-FcRI receptors on human peripheral blood granulocytes derived from the patient by:
        (1) cultivating the granulocytes in the absence of human interferon-y;
        (2) reacting the cultivated granulocytes from step (b)(1) with an immune complex comprising mouse and a chemiluminescent substance to generate chemiluminescence; and
        (3) measuring intensity of the chemiluminescence generated;
    (c) calculating a CL ratio, which is the ratio of the intensity of the chemiluminescence generated in step (b) to the intensity of the chemiluminescence generated in step (a); and
    (d) comparing the CL ratio obtained in step (c) to a CL ratio of a healthy human subject, and comparing the CL ratios for each of the samples, so as to determine whether the infectious or inflammatory disease is being cured.

* * * * *

UNITED STATES PATENT AND TRADEMARK OFFICE
CERTIFICATE OF CORRECTION

PATENT NO.    : 6,475,748 B1
DATED         : November 5, 2002
INVENTOR(S)   : Majima et al.

It is certified that error appears in the above-identified patent and that said Letters Patent is hereby corrected as shown below:

<u>Column 5,</u>
Lines 41 and 51, please correct in both lines, "human interferon-y;" to
-- human interferon-Υ; --

<u>Column 6,</u>
Lines 35 and 45, please correct in both lines, "human interferon-y;" to
-- human interferon-Υ; --

Signed and Sealed this

Twenty-ninth Day of April, 2003

JAMES E. ROGAN
*Director of the United States Patent and Trademark Office*